United States Patent [19]
Nardi

[11] Patent Number: 5,030,195
[45] Date of Patent: Jul. 9, 1991

[54] RADIOACTIVE SEED PATCH FOR PROPHYLACTIC THERAPY

[76] Inventor: George L. Nardi, 67 Mt. Vernon St., Boston, Mass. 02108

[21] Appl. No.: 361,146
[22] Filed: Jun. 5, 1989
[51] Int. Cl.$^5$ ....................... A61M 36/00; A61M 5/00
[52] U.S. Cl. ........................................... 600/7; 600/8
[58] Field of Search ............................... 600/1, 3, 6, 8; 128/654

[56] References Cited

U.S. PATENT DOCUMENTS 3,811,426  5/1974  Culver et al. ........................... 600/3
4,754,745  7/1988  Horowitz ................................ 600/8

Primary Examiner—Randall L. Green
Assistant Examiner—K. M. Reichle
Attorney, Agent, or Firm—John P. McGonagle

[57] ABSTRACT

A low-energy, nonabsorbable radioactive seed patch method and apparatus for use in conjunction with surgical procedures for prevention of reoccurrence of carcinoma and other type tumors. The patch is a nonabsorbable, plastic mesh with iodine-125 seeds threaded therein according to a predetermined pattern. The mesh with seeds threaded therein is then embedded in a nonabsorbable silicone forming the completed patch. The patch is permanently implanted over the area of potential residual cancer following surgery.

10 Claims, 5 Drawing Sheets

RADIOACTIVE SEED PATCH FOR PROPHYLACTIC THERAPY

BACKGROUND OF THE INVENTION

This invention relates to radioactive seed patches, and more particularly to its use as an implant for prophylactic cancer therapy.

Interstitial radiation therapy for use in tumor and cancer therapy has a long history. Metal needles, i.e. seeds, encapsulating radioactive isotopes have long been used to treat tumors. Since 1965 the use of Iodine-125 seeds has provided a low-energy brachytherapy source, the use of which results in reduced radiation exposure to medical personnel, patients and their families. With seeds of Iodine-125 encapsulated in a material such as titanium, shielding is provided by the surrounding tissue and the seeds can be left in the patient permanently.

A number of techniques have been developed for handling the radioactive seeds. In one technique, hollow metal needles are inserted into the tumor and the seeds are thereafter inserted into the needles while the needles are being retracted to deposit the seeds in the tumor. However, the use of needles has disadvantages and problems. Since the implant is performed through an open surgical wound, the needles can only be placed straight in a straight line or at an angle dictated by the relationship of the incision to the tumor.

Another disadvantage of the above technique is that the seeds are deposited in a track made by the needle. When the needle is withdrawn, there is a tendency for the seeds to migrate in that track resulting in a poor distribution of the seeds. Poor distribution of seeds can result in undesirable concentrations of seeds resulting in either an overdosage or underdosage of radiation.

Another disadvantage to the above technique is that the seeds are small, i.e. in the order of 4.5 mm in length and 0.8 mm in diameter. The seed is small because it must fit in small bore needles which minimally change or damage tissue. The seed has a high seed surface dose and is difficult to handle because of its small size and can be easily lost and difficult to label. In addition, the technique of implantation of individual seeds is time consuming.

In another technique, plastic catheters or threads are sutured on or in the area to be treated and seeds placed therein by insertion of a nylon tube carrying the seeds. After the desired treatment period, the nylon tubes are removed. The problem with this technique is that the catheters are difficult to place so as to provide the proper dose distribution. It is also difficult to accurately space the catheters in parallel array over irregular surfaces and to anchor the catheters to the tissue. Irregular spacing can result in radiation overdose or underdose. Also, where the ends of the catheters are brought to the surface of the skin and sutured in place, there is an incipient source of contamination.

U.S. Pat. No. 4,754,745 to B. S. Horowitz discloses another technique. Horowitz discloses a conformable sheet of material which is absorbable in living tissue and has a plurality of radioactive seeds in a predetermined array within the sheet. The fundamental problem with the Horowitz technique is that the seed holder is absorbable. Horowitz's sheet material is absorbable in a period of from about 70 to 120 days. However, the iodine-125 needles used with the sheet are radioactive for approximately one year. When the sheet is absorbed into the tissue, there is nothing but tissue to hold the radioactive needles in place. This will permit some seed migration within the tissue and can result in undesirable concentrations of seeds resulting in either an overdosage or underdosage of radiation.

SUMMARY OF THE INVENTION

The purpose of the present invention is to provide a radioactive seed patch method and apparatus for use in conjunction with surgical procedures for the prevention of reoccurrence of carcinomas and other type tumors.

In many instances where tumors are removed, there is often residual microscopic disease. For example, in the case of pancreatic carcinoma, over 50% of patients succumb with locally recurrent disease after a tumor is removed. To optimize control of this disease, applicant has developed a "MARLEX" ® silicone iodine implant which is a permanent implant placed into the area of potential residual cancer following surgery. The primary purpose of the instant invention is to provide low-energy, surface radiation and very thin penetration of normal tissue for prophylactic therapy and to minimize any damage to normal tissue. The radioactive seed patch is put in place during the time of surgery after resection of the tumor to eliminate residual cancer cells and to prevent recurrence of the cancer. Applicant's patch is nonabsorbable and consequently the seeds cannot migrate or be displaced as they would if embedded in an absorbable material.

Other and further objects, as well as various advantages and features of novelty which characterize the invention are pointed out with particularity in the claims annexed hereto and forming a part hereof. However, for a better understanding of the invention, its advantages and objects obtained by its use, reference should be had to the drawings which form a further part hereof, and to the accompanying descriptive matter in which there is illustrated and described a preferred embodiment of the invention.

DETAILED DESCRIPTION OF THE INVENTION

Figure 1:
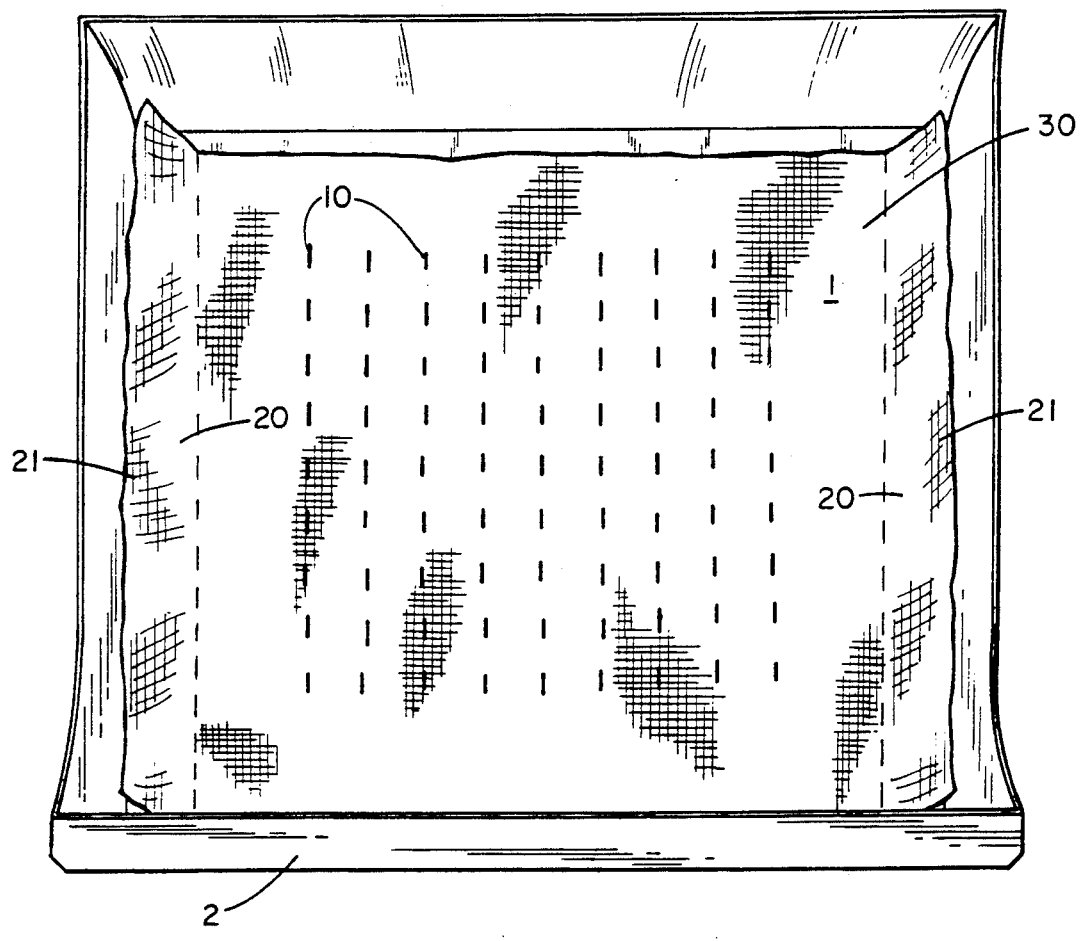
FIG. 1 is a face view of one embodiment of the radioactive seed patch of the present invention.
Figure 2:
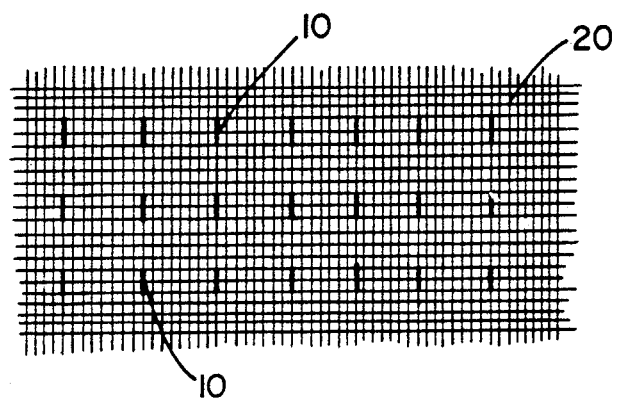
FIG. 2 is a plan view thereof.
Figure 3:
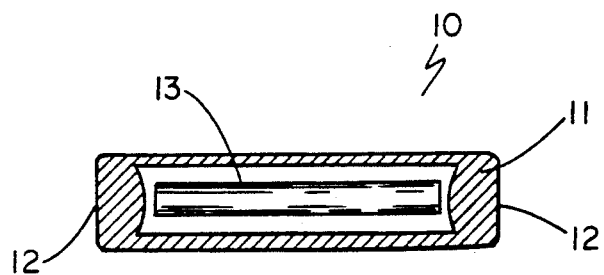
FIG. 3 is an enlarged sectional view of a typical seed utilized in the invention.

Referring to the drawings in detail wherein like numerals indicate like elements, reference numeral 1 refers to a generally rectangular patch constructed in accordance with the present invention. Radioactive seeds 10 are threaded according to a predetermined pattern into a plastic mesh 20 such as "MARLEX" ® which is a polypropylene mesh. The mesh 20 containing the seeds 10 is then embedded in a nonabsorbable silicone 30, such as "SILASTIC" ®. The "SILASTIC" ® 30 fixes the seeds 10 within the mesh 20 and permanently prevents their displacement even when the mesh 20 is flexed over curved surfaces. Another type of plastic which could be used in place of the "MARLEX" ®, is "GORETEX" ®. The seeds 10 could be threaded into a "GORETEX" ® mesh 20 just as well and the entirety enclosed in "SILASTIC" ® 30. The choice of the "MARLEX" ® was due to it being more of a mesh and more easily threadable. It is also far cheaper and more generally available.

All three materials, i.e., "SILASTIC" ®, "MARLEX" ®, and "GORETEX" ®, are nonabsorbable and have been approved by the FDA for biological use. They are used widely. For example, a standard repair for hernias, the most common surgical operation, involves the use of "MARLEX" ® or "GORETEX" ® as a reinforcing layer and thousands of these patches have been used throughout the world.

The "SILASTIC" ® 30 embedding guarantees that the seeds 10 will not move. This is the criticism of the Horowitz patch which is made up of an absorbable compound. The Horowitz material is resorbed at various rates within the body, usually a matter of months. Yet the seeds remain active and radiation continues for a year or more. It is possible that with absorption of the material or even partial absorption of the material some of the seeds would be free to move around and create a concentration of radiation in one spot and a lack of radiation in another thus causing both dangers or local overdosage and areas of inadequate treatment.

The seeds 10 used in this invention are iodine-125 seeds and range from 4.2 to 4.9 mm in length and from 0.77 to 0.96 mm in diameter. The shell material 11 is titanium tubing having a wall thickness of 0.05 mm with welds at both ends 12. The seed 10 used in the preferred embodiment contains within it a silver rod 13 serving both as an X-ray marker and a carrier for iodine-125. Iodine-125 has a half-life of 59.6 days. The energy of the iodine-125 is 27-35 keV and has a half value in a tissue layer of 2 cm.

The method which would be followed for use of the invention is as follows. The exact location and extent of the tumor is determined. The tumor is surgically removed. Following removal of the tumor, a sterile, nonabsorbable radioactive seed patch 1 is tailored, positioned and sutured over the region where there may be remaining cancer cells. The patch 1 will be permanent and would not be removed unless necessary.

A postmortem performed on the first patient who received the radioactive seed patch implant indicated that there were no adverse effects from the implant. The patient had a tumor removed in the head of the pancreas and the patch implanted over the resected area. The patient died from liver complications related to pancreatic carcinoma.

Figure 4:
FIG. 4 is an X-ray of a patient with a radioactive seed patch in place over his pancreas after tumor removal.
Figure 5:
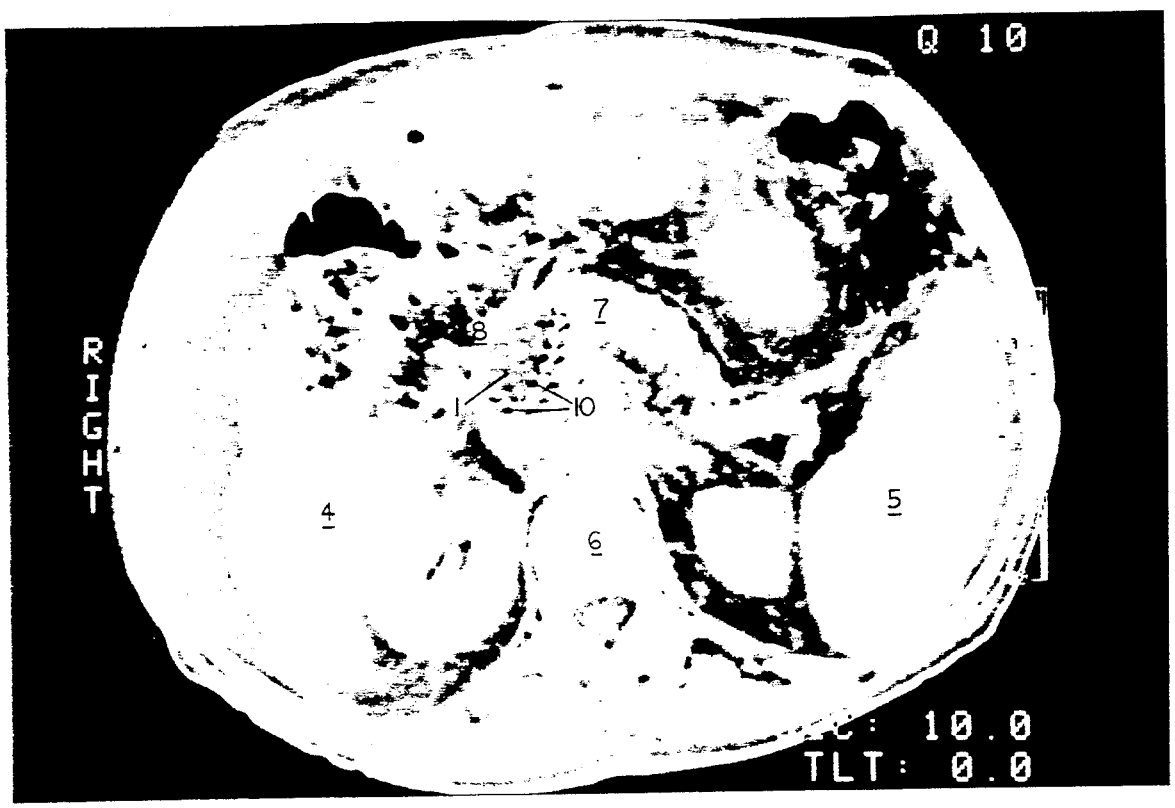
FIG. 5 is a cross section CAT scan of the same patient.
Figure 6:
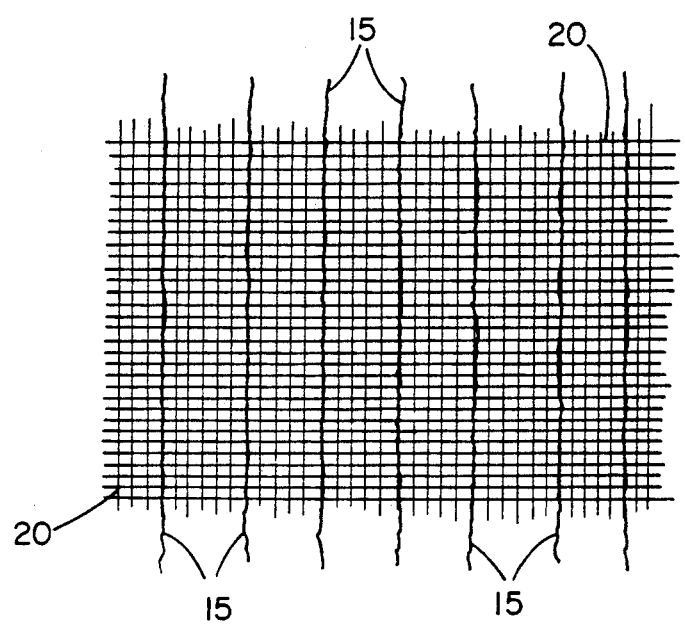

FIG. 1 is a face view of the radioactive seed patch 1 in a shielded container 2 prior to its use in surgery. As may be seen from this Figure, the side edges 21 of the mesh 20 have not been embedded in silicone 30. The silicone embedding procedure is accomplished directly in the shielded container 2 itself prior to shipment. The portion of the mesh 20 not embedded in silicone is cut off before implanting. FIG. 4 is an X-ray of a patient with a radioactive seed patch 1 implanted. Because of the silver rod 13 within each seed 10, the seeds 10 are readily visible on the X-ray. FIG. 5 is a cross section CAT scan of the same patient. Visible for orientation purposes is the patient's liver 4, spleen 5, spine 6, and the pancreas 7. It may be noted that the right lobe 8 of the pancreas 7 has been removed. A radioactive seed patch 1 was implanted over the surgical removed area. The radioactive seeds 10 may be seen.

Other embodiments may be readily devised by those skilled in the art which will embody the principles of the invention and fall within the spirit and scope thereof. In one variation the seeds may be replaced with radioactive threads 15 threaded through the mesh 20.

I claim:

1. A radioactive seed patch for prophylactic therapy, comprising:
    a nonabsorbable mesh;
    a plurality of nonabsorbable radioactive seeds threaded into said mesh in a predetermined pattern; and
    wherein said mesh containing said seeds is embedded in a nonabsorbable silicone.

2. A patch as recited in claim 1 wherein:
    said mesh is a plastic mesh.

3. A patch as recited in claim 2 wherein:
    said seeds have a generally cylindrical shape.

4. A patch as recited in claim 3 wherein:
    said seeds contain a low-energy isotope.

5. A patch as recited in claim 4 wherein:
    said low-energy isotope is contain iodine-125.

6. A radioactive seed patch for prophylactic therapy, comprising:
    a nonabsorbable mesh;
    a plurality of nonabsorbable radioactive threads threaded into said mesh in a predetermined pattern; and
    wherein said mesh containing said threads is embedded in a nonabsorbable silicone.

7. A patch as recited in claim 6 wherein:
    said mesh is a plastic mesh.

8. A method for prophylactic therapy comprising:
    determining the exact location and extent of a tumor;
    removing the tumor by proper surgical technique;
    positioning a sterile nonabsorbable mesh containing a plurality of radioactive elements threaded into said mesh in a predetermined pattern, the mesh with elements threaded therein being embedded in a nonabsorbable silicone, over the region where there may be residual cancer cells;
    suturing the mesh in place; and
    closing the surgical incision.

9. A method in accordance with claim 8 wherein:
    said elements are seeds.

10. A method in accordance with claim 8 wherein:
    said elements are threads.

* * * * *